United States Patent
Thomas et al.

(10) Patent No.: US 8,040,502 B2
(45) Date of Patent: Oct. 18, 2011

(54) OPTICAL INSPECTION OF FLAT MEDIA USING DIRECT IMAGE TECHNOLOGY

(75) Inventors: David P. Thomas, Unionville (CA); Adam Weiss, Pickering (CA)

(73) Assignee: WDI Wise Device Inc., Markham, ON (CA)

( * ) Notice: Subject to any disclaimer, the term of this patent is extended or adjusted under 35 U.S.C. 154(b) by 690 days.

(21) Appl. No.: 11/575,437

(22) PCT Filed: Sep. 19, 2005

(86) PCT No.: PCT/CA2005/001421
§ 371 (c)(1),
(2), (4) Date: Mar. 16, 2007

(87) PCT Pub. No.: WO2006/029536
PCT Pub. Date: Mar. 23, 2006

(65) Prior Publication Data
US 2008/0062422 A1    Mar. 13, 2008

Related U.S. Application Data

(60) Provisional application No. 60/610,605, filed on Sep. 17, 2004.

(51) Int. Cl.
*G01N 21/00* (2006.01)
(52) U.S. Cl. .................. 356/237.2; 356/239.1
(58) Field of Classification Search ............... 356/239.1, 356/237.2
See application file for complete search history.

(56) References Cited

U.S. PATENT DOCUMENTS

| | | | |
|---|---|---|---|
| 3,814,946 A | 6/1974 | Shiro et al. | |
| 4,306,808 A * | 12/1981 | Vander Neut | 356/239.1 |
| 5,157,266 A * | 10/1992 | Schmiedl | 250/559.17 |
| 5,907,396 A * | 5/1999 | Komatsu et al. | 356/237.1 |
| 6,222,624 B1 * | 4/2001 | Yonezawa | 356/237.1 |
| 6,437,357 B1 * | 8/2002 | Weiss et al. | 250/559.4 |
| 7,142,295 B2 * | 11/2006 | Gahagan et al. | 356/237.2 |
| 2002/0186368 A1 | 12/2002 | Rosengaus et al. | |

FOREIGN PATENT DOCUMENTS

CA          2252308          4/2000
(Continued)

OTHER PUBLICATIONS

PCT International Searching Authority (ISA/CA), International Search Report and Written Opinion for PCT Publication No. WO 2006/029536, Dec. 19, 2005.

(Continued)

*Primary Examiner* — Roy M Punnoose
(74) *Attorney, Agent, or Firm* — Borden Ladner Gervais LLP; Jeffrey W. Wong

(57) ABSTRACT

The invention is directed at a method and system of detecting defects in a transparent media such as a piece of glass. The method comprises the steps of transmitting light from a light source towards the transparent media and then detecting defects in the transparent media by scanning the light as it is reflected or passes through the transparent media. The method and system may operate in any one of a dark field mode, a bright field mode for scanning or a bright field mode for inspecting.

6 Claims, 5 Drawing Sheets

FOREIGN PATENT DOCUMENTS

| | | |
|---|---|---|
| CA | 2384005 | 3/2001 |
| CA | 24370051 | 7/2002 |
| JP | 02083438 | 3/1990 |
| JP | 05087725 | 4/1993 |
| JP | 10153555 | 6/1998 |
| JP | 2002162355 | 6/2002 |
| JP | 2002529698 | 9/2002 |
| JP | 2003508786 | 3/2003 |
| JP | 20030307978 | 10/2003 |
| JP | 2005536732 | 12/2005 |
| JP | 04178545 | 6/2011 |
| WO | 2004019108 | 3/2004 |

OTHER PUBLICATIONS

European Patent Office, Extended European Search Report for EP Patent App. No. 05787648.4, Sep. 2, 2010.

Sakamoto et al., "An Algorithm for Object-Light Calculation Considering Reflectance Distribution for Computer-Generated Holograms (Three-Dimensional Image Information Media)", The Journal of the Institute of Image Formation and Television Engineers, Apr. 1, 2002, pp. 611-616, vol. 56, No. 4, The Institute of Image Information and Television Engineers, Japan.

Japanese Patent Office, Notice of Reasons for Rejection for JP Patent App. No. 2007-531555, May 19, 2011.

* cited by examiner

OPTICAL INSPECTION OF FLAT MEDIA USING DIRECT IMAGE TECHNOLOGY

FIELD OF THE INVENTION

This invention relates generally to the field of Automated Optical Inspection (AOI) of flat, non-patterned media such as glass, synthetic foil, and coated/uncoated plates. The invention in particular relates to the automated optical inspection of glass substrates used for the manufacture of Flat Panel Displays (FPDs).

BACKGROUND OF THE INVENTION

Modern, high performance flat panel displays are mostly based on Liquid Crystal (LC) technology and are often referred to as Liquid Crystal Displays (LCDs). Flat Panel Displays (FPDs) and LCDs use glass as both a substrate and a cover sheet with a thin LC layer encapsulated in-between the two sheets of glass. The glass sheets used in the manufacturing of FPDs are quite large as indicated in the table below (glass dimensions are in mm):

| Gen 5 | Gen 5.5 | Gen 6 | Gen 7 |
|---|---|---|---|
| 1000 × 1200 | 1300 × 1500 | 1500 × 1800 | 1800 × 2000 |
| 1200 × 1300 | | 1500 × 1850 | 1850 × 2100 |
| | | 1600 × 1900 | 1870 × 2200 |
| | | | 1900 × 2200 |

In particular, TV and computer FPD screens contain a large number of picture elements, i.e. pixels, with the typical pixel size for a computer screen FPD being 80×240 µm. Pixels are formed by a Thin Film Transistor (TFT) pattern, which is deposited on the substrate in multiple photo-lithography steps. Defects as small as 15×15 µm in the glass substrate, in particular pits, disrupt the TFT deposition process resulting in defective pixels or a defective TFT array. These glass defects, in the substrate or cover glass, may adversely affect the transmission of light through the finished FPD resulting in an unacceptable FPD product and adversely effect the TFT patterning process resulting in shorts, open circuit or electrically defective thin film transistors.

Some examples of glass defects include a pit which is a small indentation in the glass; an inclusion or embedded foreign particle, such as platinum, stainless steel, silica or a gas bubble; an adhesion chip, such as a glass chip fused with the glass surface and not removable by washing; a scratch; and edge chip; or a distortion, such as a localized refractive index non-uniformity or a localized error of flatness/thickness which introduces an undesirable lens like effect to the substrate. These defects vary in shape, and may range in size from ~15×15 µm to a few hundred microns.

The discovery of defects in a final inspection of FPD panels is troublesome, due to the high material and labour costs of manufacturing a defective FPD. Therefore, it would be beneficial for the glass manufacturer to inspect the glass prior to shipping it to FPD fabrication plants.

Known methods of inspecting large, flat, non-patterned media typically fall into two main categories: (a) imaging systems using an imaging element, such as a charge coupled device or CCD, with pixels of a smaller size than required by the inspection resolution (object plane resolution) and an imaging lens to provide optical magnification to match the camera pixel size to a desired object plane resolution or (b) laser scanners using a laser beam focused down to the spot size corresponding to the desired object plane resolution and a single detector.

Prior art related to the category imaging methods includes U.S. Pat. No. 6,633,377 entitled Dark View Inspection System for Transparent Media; U.S. Pat. No. 6,437,357 entitled Glass Inspection System including Bright Field and Dark Field Illumination; U.S. Pat. No. 6,208,412 entitled Method and apparatus for determining optical quality; U.S. Pat. No. 5,642,198 entitled Method of Inspecting Moving Material; and U.S. Pat. No. 5,493,123 entitled Surface Defect Inspection System and Method. Typically, for web inspection, line scan CCD cameras are used with the camera pixel size ranging from 7 µm to 13 µm. Cameras of 7 µm pixel size and 8 kilo-pixels (8192) resolution are commercially available. In order to achieve a desired defect detection accuracy of 15×15 µm, the object plane resolution of the imaging system should be at least 20×20 µm yielding a lens magnification of 20 µm/7 µm=2.85. If the object plane size is 2,000 mm, the total number of pixels in the object plane is 2,000 mm/20 µm=100,000 and thus the required number of cameras is 100,000/8 kpixels=13. When taking into consideration the expense of thirteen 8 k CCD cameras, the total cost of the inspection systems based on line scan cameras is very high.

Moreover it is difficult and costly to provide CCD camera system with a lens that does not limit the camera pixel resolution, in particular for a large CCD sensor size of 0.007 mm×8,192=57.4 mm. If an ideal diffraction limited lens is used with the 8 k camera, the required F-number would be 3.3, which is on the boundary of practicality to design the lens with an image plane size of 57.4 mm, F-number of 3.3 and optical point spread function (PSF) of 7 µm across the entire field of view—even for monochromatic light application. In practice the lens PSF limits the imaging system performance by limiting the resultant optical resolution. Conversely if one attempts to apply a 13 µm pixel size camera, the required F-number for an ideal lens would be 5, which is less demanding. Due to silicon die size limitations, these types of cameras are typically only available with a 2 k (2024) pixel resolution. In this case, to cover the object plane of 2,000 mm one would require 50 cameras, making an inspection system prohibitively expensive. Therefore, when using small CCD pixel size, optics limit the resultant imaging system resolution and when using large CCD pixel size, the result is a prohibitively large number of cameras.

Prior art related to the laser scanning methods includes U.S. Pat. No. 5,452,079 entitled Method of and Apparatus for Detecting Defect of Transparent Sheet as Sheet Glass. The limiting performance-cost product of a typical CCD based optical imaging system can be overcome by utilizing an optical scanner.

One disadvantage of using optical scanners for LCD glass inspection is a scanning speed limitation imposed by the scanner mechanics. Another disadvantage is that, in order to maintain a web speed of 100 mm/s, multiple scanners are required. Furthermore, a single optical scanner is unable to cover a glass width of 2000 mm. Therefore, multiple scanners are required, which increases the cost of the inspection system.

It is, therefore, desirable to provide a novel method and apparatus for inspecting flat media.

SUMMARY OF THE INVENTION

It is an object of the present invention to obviate or mitigate at least one disadvantage of previous media inspection methods. Typically, the inspected objects exhibit uniform optical properties and may be transparent, opaque, reflective (specular) or diffuse.

In a first aspect of the present invention there is provided a method of detecting flaws in a transparent object. The method includes the steps of selecting at least two of a dark field scanning mode, a bright field scanning mode for inspecting reflective media and a bright field mode for inspecting the surface of transparent media; scanning the transparent object using the at least two selected scanning modes using a contact image sensor; and combining the results of the at least two scans to provide a mapping of at least one of top surface scratches, pitting distortions, inclusions, adhesion chips and top surface dust. In an embodiment of the present invention the step of scanning the transparent object includes sequentially scanning the object using each of the at least two selected scanning modes.

In one aspect of the invention, there is provided microscopy level (15 um) defect detection accuracy over a field of view as large as over 2 meters.

In another aspect, there is provided a more reliable means of discriminating true defects from harmless airborne particles attracted onto the glass.

In yet a further aspect, there is provided a more reliable defect size assessment than inspection systems of the prior art.

In another aspect, there is provided a means of inspecting the glass while it is in motion on a conveyor, preferably at the speed of 100 mm/s.

Another aspect of the present invention provides a system for carrying out the above method, the system comprising a GRIN lens array, LED illumination array and a CMOS photodiode array.

In a further aspect, there is provided apparatus for detecting defects in a transparent media comprising lighting means for providing collimated light to said transparent media; and means for scanning said transparent media as said light reflects off of or passes through said transparent media and for storing and displaying an image associated with said scans, preferably with defective areas only.

In yet another aspect, there is provided a method of detecting defects in a transparent media comprising the steps of transmitting collimated light from a light source to said transparent media; scanning said transparent media as said collimated light reflects off or passes through said transparent media; storing results of said step of scanning; and displaying said results as a mapping of said transparent media.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Generally, the present invention provides a method and system for automated optical inspection of glass substrates. As will be known by one skilled in the art of optics, Gradient Refractive INdex (GRIN) lens arrays are capable of image transfer from an object plane to the image plane with a unity magnification. The images produced by the GRIN lens arrays are erect and reproduced with very high fidelity, have no distortion at their periphery, a uniform resolution and an even brightness. High performance GRIN lens arrays are typically characterized by a point spread function at the level of 20 μm. GRIN lens arrays are typically used by document scanners, where a large field of view is required and imaging has to be performed with high resolution. Assemblies combining a GRIN lens array, a LED illumination array and a CMOS photodiode array are commercially available and are often referred to as Contact Image Sensors (CIS). The CIS is a key component of low cost, high resolution (up to 2400 dots per inch) optical document scanners.

Figure 1:
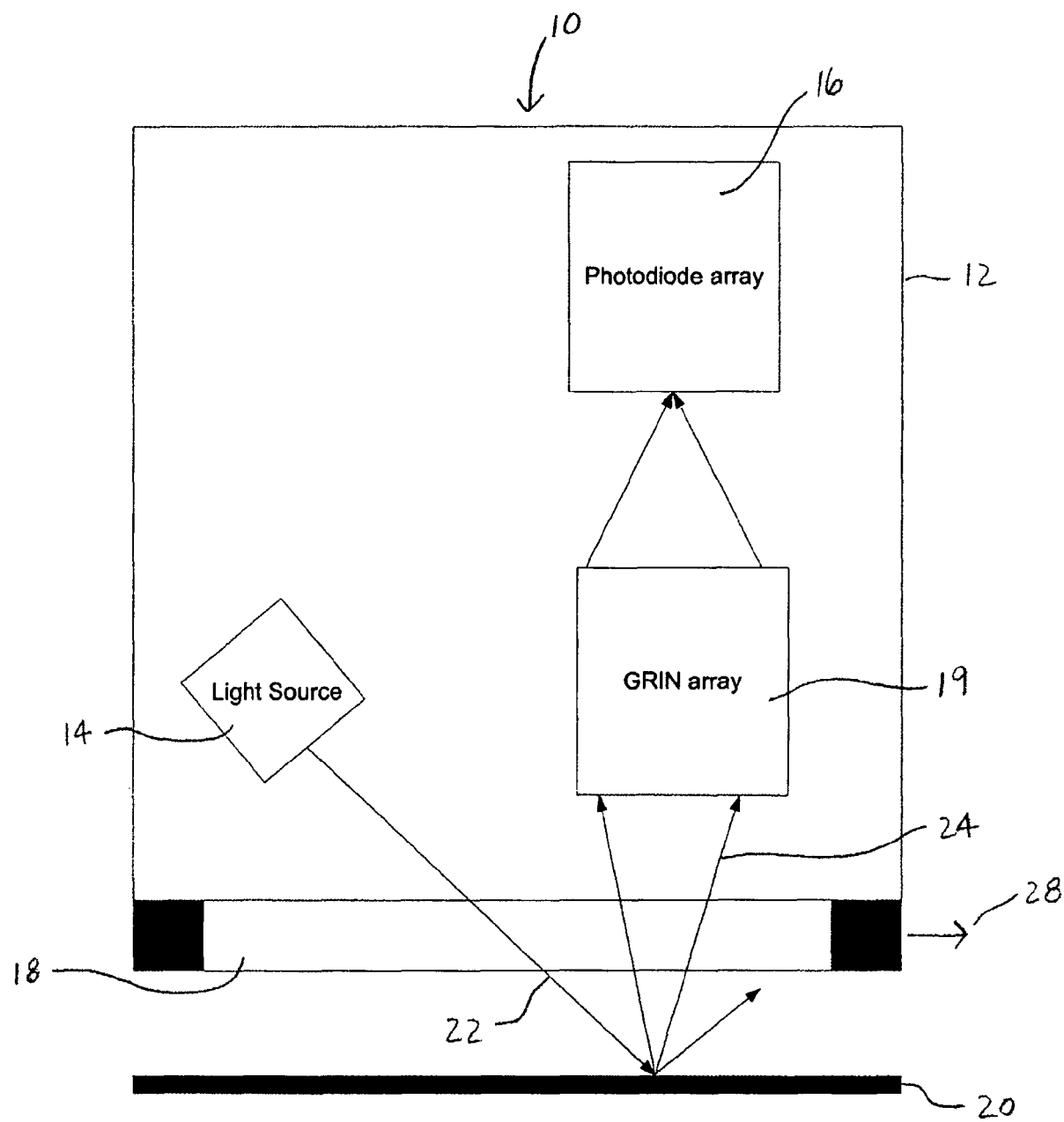
FIG. 1 is a schematic view of a of a typical contact image sensor (CIS)

A typical CIS is schematically shown in FIG. 1. The CIS 10 comprises a CIS housing 12 housing a Light Emitting Diode (LED) array 14 with collimating optics, a complementary metal-oxide-semiconductor (CMOS) photodiode array 16 and a GRIN lenslet array 19. The housing 12 also comprises a protective glass window 18 located at the bottom of the housing 12. An object to be scanned 20 is placed beneath the housing 12, preferably parallel and aligned with the protective glass window 18, so that the light from the LED array 14 may pass through the glass window 18 and be scattered off the object to be scanned 20.

In operation, light is transmitted from the LED array 14 through the protective glass window 18 and GRIN lens array 19 to the object to be scanned 20 as shown by arrow 22. The light scatters, off the object to be scanned 20 back towards the protective glass window 18 and GRIN lens array 19 as indicated by arrows 24. The scattered light enters back into the housing 10, and after passing through the GRIN lens array 19, produces an image on the CMOS photodiode array 16, which in turn converts the image into its electrical representation suitable for recording it in a digital form and—if required—processing it by means of software. The CIS generally moves uniformly in the direction of arrow 28 so that light is scattered off each part of the object to be scanned 20, such that the entire scanned image is acquired line by line by the CMOS array 16.

In its unaltered optical setup, the CIS 10 may be used for inspection of opaque diffusing flat media. However, since most commercial CIS 10 only scan at speeds of 5 to 10 mm/s, it is desirable to increase the scanning speed. The speed of CIS scanning can be substantially improved by reading in parallel a multitude of small segments of the CMOS photodiode array. Those fluent in the field refer to these segments as photodiode array taps. For a typical CIS sensor with 1200 dpi resolution and 3 MHz pixel clock, 15 taps are required to enable it to scan at 100 mm/s.

The contact image sensor is adaptable to flat media inspection. It can be made to operate in different modes such as a dark field mode for inspecting reflective media, such as LCD glass; a bright field mode for inspecting transparent media, such as LCD glass; or a bright field mode for inspecting surface only of the transparent media, such as LCD glass.

Figure 2:
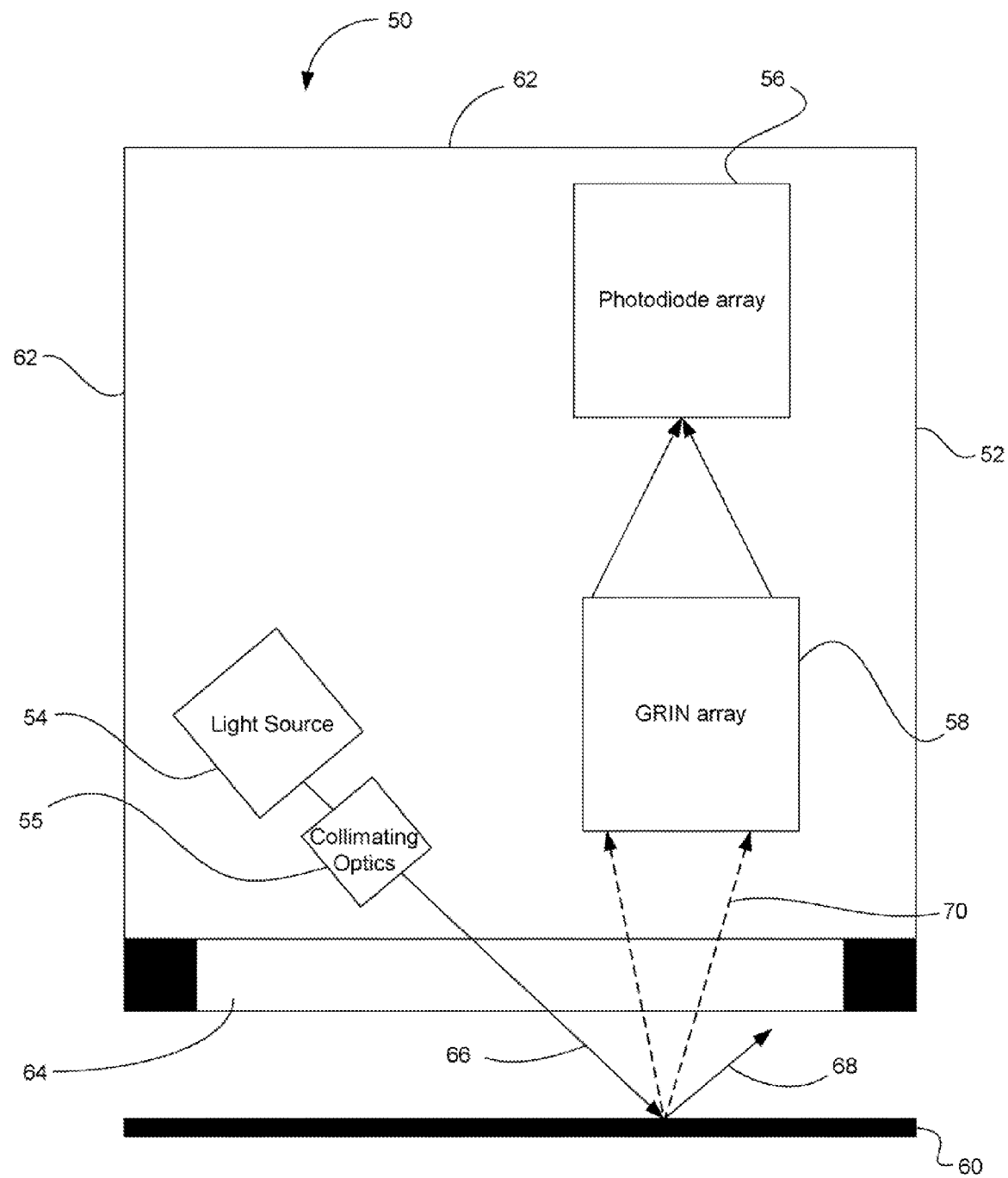
FIG. 2 is a schematic view of an embodiment of apparatus for inspecting flat media in a dark field inspection module in accordance with the invention.

Turning to FIG. 2, a schematic diagram of an embodiment of the invention is shown. In this embodiment, apparatus for optical inspection of flat media in a dark field mode is shown. The apparatus 50 comprises a housing 52 which houses a light emitting diode (LED) array 54, with collimating optics 55 along with a photodiode array, preferably a CMOS linear photodiode array, 56 along with a GRIN lens array 58. The apparatus 50 is used to inspect a flat media, which in this embodiment is preferably a sheet of LCD glass 60, an unpatterned opaque material or the like, to determine whether or not there are defects in the top surface of the flat media 60. The light source 54 is preferably situated at an oblique angle with respect to the object to be scanned, such as the sheet of LCD glass 60.

The housing 50 preferably comprises five (5) opaque walls 62 and a transparent sixth wall 64, preferably in the form of a glass window.

In operation, a sheet of collimated light (indicated by arrow 66) is transmitted from the LED array 54 towards the sheet of LCD glass 60 through the glass window 64. Due to the position of the light source 54 with respect to the sheet of glass 60, if the LCD glass is defect-free, the sheet of collimated light then reflects off the LCD glass 60 away from the GRIN lens array entry aperture, as indicated by the ray (seen as arrow 68). In this manner, no image is formed on the photodiode array 56 and the image remains dark. However, if a defect is present on the surface of the media being inspected 60, the defect scatters the incident light 66 and thus diverts it towards an entry aperture of the GRIN lens array 58 as schematically depicted by the dashed lines 70. The presence of light at the lens array 58 causes a bright image to be formed on the photodiode array 56 indicating the presence of the defect. Since the inspection is performed on a line-by-line basis the location, as well as the presence, of the defect on the sheet of LCD glass 60 may also be easily determined. The location is important since the defect may not be visible to the naked eye.

In the dark field mode of operation, the apparatus 50 is capable of capturing defects within the lens array depth of field, which is usually not more then 50 um (for 1200 dpi CIS). In other words, the defects are detected on the surface down to a depth of ~50 um.

Figure 3A:
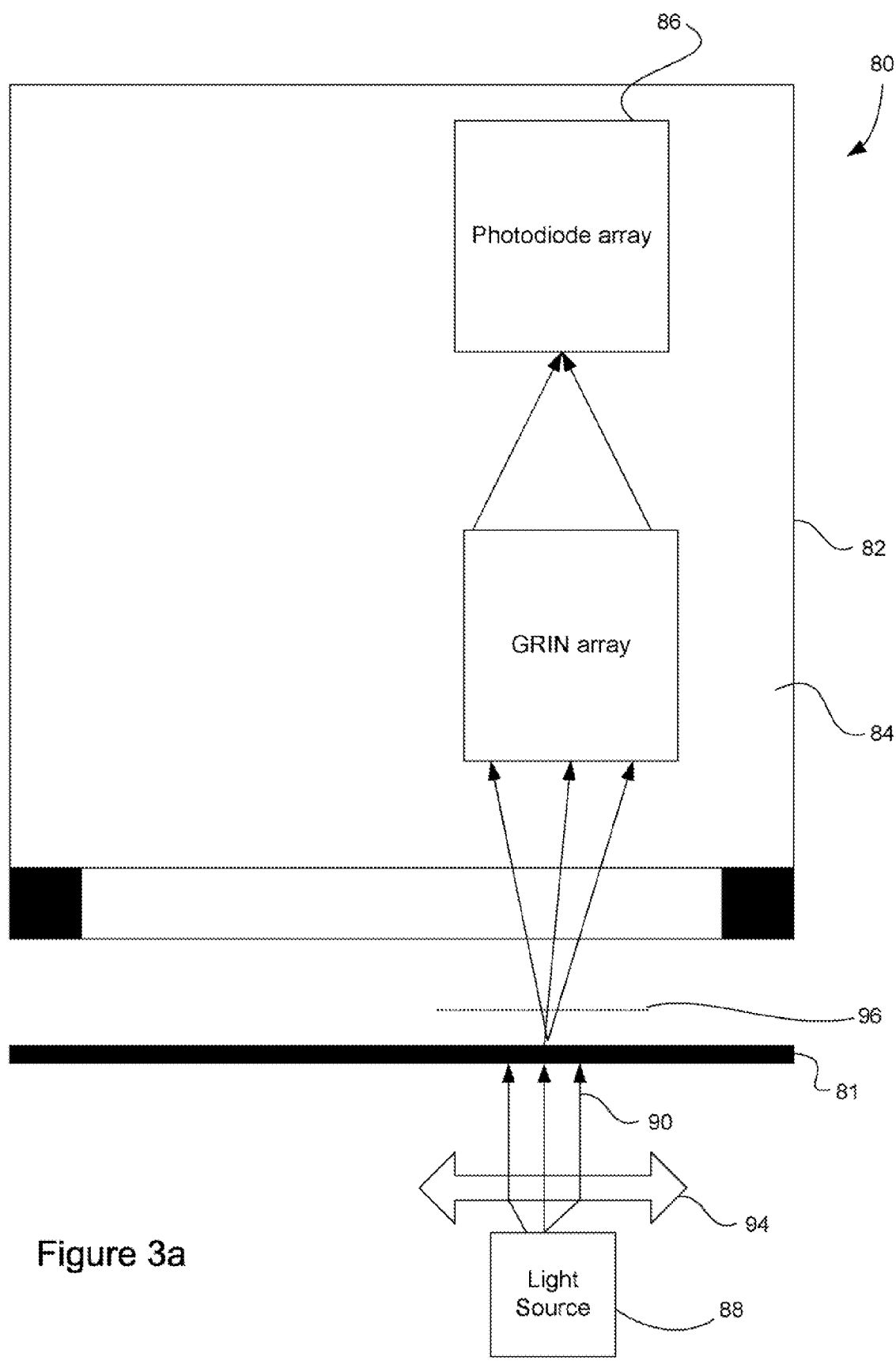
FIG. 3a is a schematic view of an embodiment of apparatus for inspecting flat media as a bright field inspection module in accordance with the invention.

In another embodiment, as shown in FIG. 3a, apparatus 80 for inspecting a flat media, such as a piece of glass 81, comprises a housing 82 which houses a GRIN lens array 84 and a photodiode array, preferably CMOS, 86. The apparatus 80 further comprises a light source 88 which is located remote from the housing 82. In this bright field mode of operation, the glass 81 is illuminated from the bottom with a collimated sheet of light (seen as arrows 90) from the light source 88. The light from the light source 88 is collimated by a collimator assembly 94. In the bright field mode, the piece of glass 81 acts as a transparency and any defects in the glass 81 block the light from passing through. The light that passes through the glass 81 produces an image which is then formed on a mild film diffuser 96 located between the glass 81 and the housing 82. This image is then picked up by the lens 84 and consequently projected onto the photodiode array 86 for detection. A review of the image projected onto the photodiode array allows a user to determine if there are any defects in the piece of glass 81.

Figure 3B:
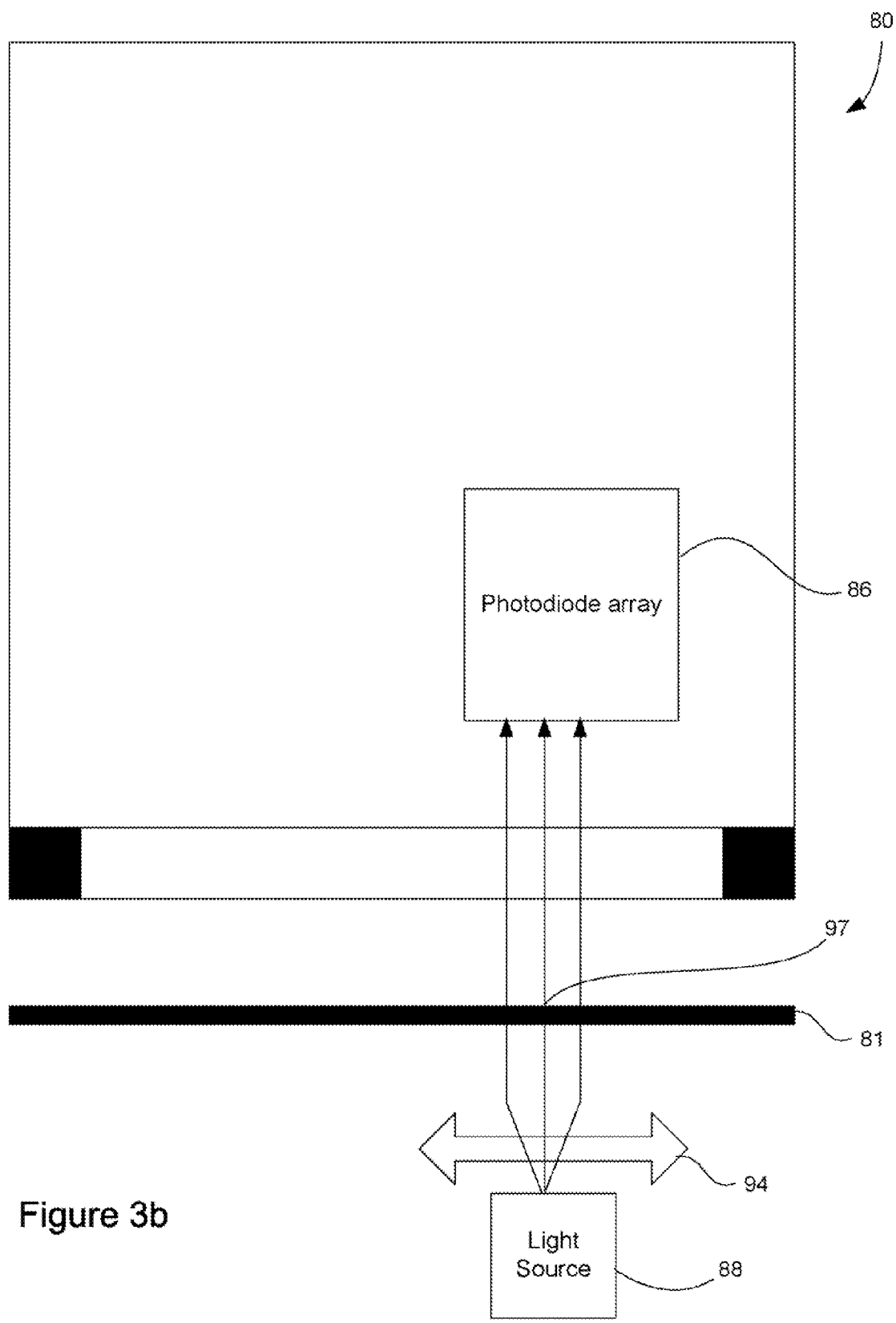
FIG. 3b is a schematic view of another embodiment of apparatus for inspecting flat media as a bright field inspection module in accordance with the invention.

In a further embodiment, as shown in FIG. 3b, the light that passes through the glass is formed directly, without any lenses, onto the photodiode array 86. The light source 88 is preferably a single LED, or other incoherent illumination semi-point source. The signal to noise ratio in the image is improved by reducing or preventing the creation of interference fringes due to the interaction of light reflected between the top and bottom surfaces of the glass 81. Furthermore, the light source 88 is preferably a blue LED array to provide a further advantage over prior art systems, since the short wavelength illumination promotes diffraction on small defects which assist in accurately determining the size of a defect. In this embodiment, the mode of operation is analogues to the principle of photolithography, where the mask is replaced by the piece of glass 81 with defects and the photo-resist with the mild film diffuser 96 (FIG. 3a) or a focal plane array 97 (FIG. 3b). Any defects block the light from passing through the piece of glass 81 and appear as spots, surrounded by a diffraction pattern, on the photodiode array 86.

In operation, light from the light source 88 passes through the collimator assembly 94 and is collimated. The collimated light then passes through the glass 81 to the diffuser 96. The presence of defects in the glass 81 prevents the collimated light from passing through the glass 81. The light which passes the glass then forms an image on the photodiode array 86. This image is then displayed as a mapping of the glass to display defects in the glass.

In the case of small defects (between 15 and 50 μm), their image size is strongly affected by light diffraction and appear enlarged and surrounded by diffraction rings. However use of a diffraction model, such as the Kirhoff-Fresnel or Fraunhoffer diffraction model, allows the actual size of the defect to be estimated. By having the enlarged defect images, the calculation of the diffraction model is facilitated.

The bright field mode of operation is effective in not only detecting light blocking defects, but also defects exhibiting optical power, such as pits, which act like a negative micro lens, or localized refractive index variations or a localized error of flatness/thickness, which divert light away from the diffusing film and thus are detected as dark spots surrounded by a bright halo. Since the bright field illuminator is focused to infinity, the depth of field is limited by light diffraction on the defects to be detected and is not less then 2 mm for defects of 20×20 μm.

Figure 4:
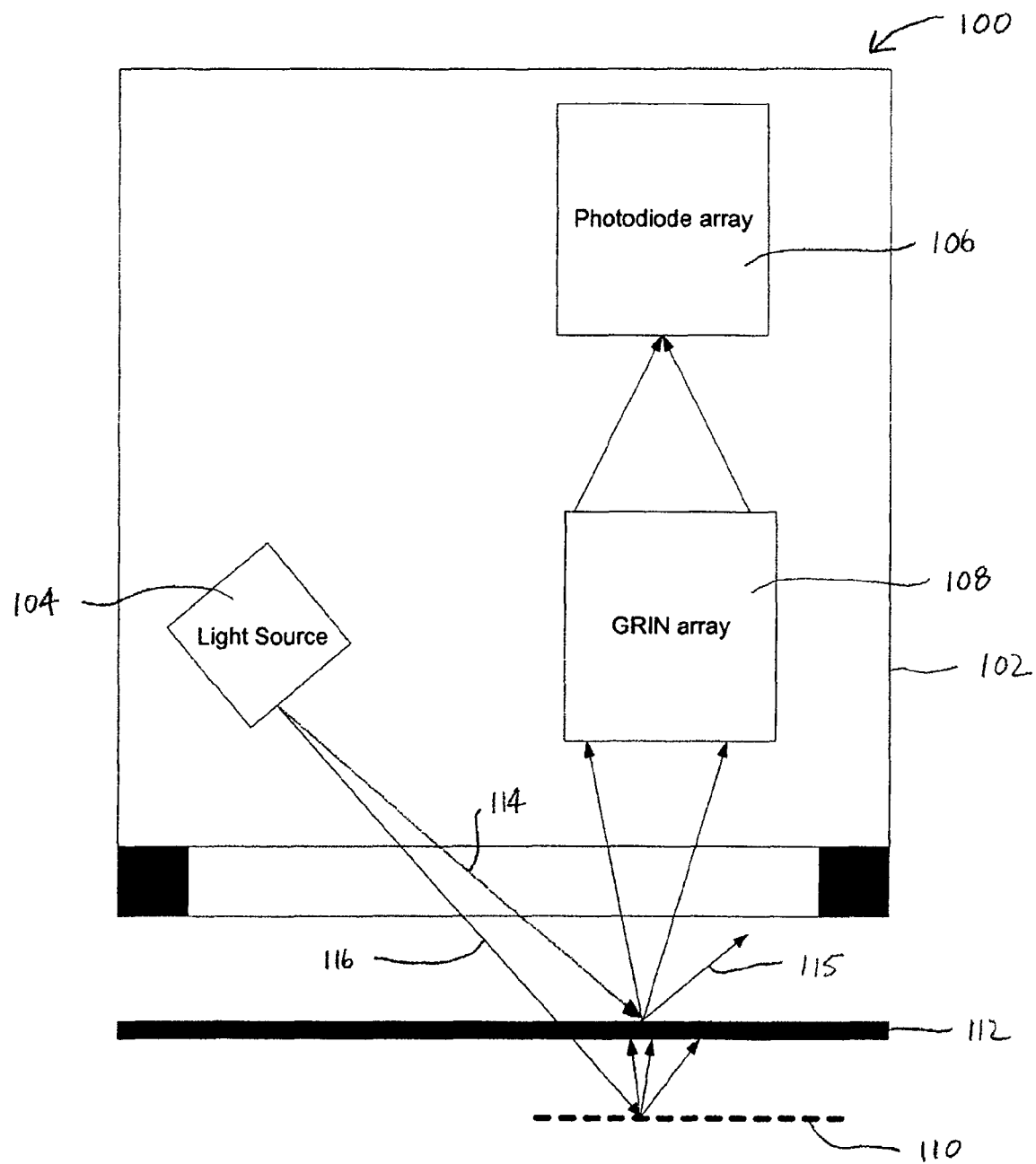
FIG. 4 is a schematic view of another embodiment of apparatus for inspecting flat media using a bright field set up for inspecting top surface of glass specimen in accordance with the invention.

Turning to FIG. 4, an apparatus for inspecting a surface of transparent media in a bright field mode is shown. The apparatus 100 comprises a housing 102, which houses a light emitting diode (LED) array 104 with collimating optics, a, preferably CMOS, photodiode array 106 and a GRIN lens array 108. The apparatus 100 further comprises a light diffusing surface 110, which is placed below a piece of transparent media 112, such an LCD glass to be examined.

During the inspection process, light rays (illustrated as arrows 114) from the LED array 104 are transmitted toward the transparent media 112 and reflected away (arrow 115) from the GRIN lens array 108. These rays are not registered by the photodiode array 106. Other light rays 116, from the LED array 104, pass through the media 112 and are scattered by the light diffusing surface 110. These light rays then pass back through the transparent media 112 thereby illuminating it. Some of the light rays are transmitted to the GRIN array 108 to produce an image which is then transmitted to the photodiode array 106. The GRIN lens array's depth of field is preferably approximately 50 μm, and therefore only the defects from the top surface of the glass and those embedded no deeper than the depth of field (~50 μm) of the GRIN lens array 108 are legibly detected by the photodiode array 106. Since the illuminating beam of light originates from the diffusing surface 110 and thus is not collimated, defects with optical power, such as pits, are not registered.

As will be understood, the three embodiments disclosed above, may be implemented individually into a glass inspection system according to the inspection objectives. For instance if only the top surface of glass needs to be inspected, the embodiments of FIGS. 2a and 2b may be adopted.

Furthermore, multiple embodiments/modes of operation may be combined together in one instrument providing a more powerful means of defect classification by cross-referencing the defect image intensity registered by inspection modules operating in different inspection modes. Properties of the embodiments are shown below with Mode A representing the embodiment of FIG. 2a, Mode B representing the embodiment of FIG. 2b and Mode C representing the embodiment of FIG. 3.

| Defect type | Image intensity | | |
| --- | --- | --- | --- |
| | Mode A | Mode B | Mode C |
| Top surface scratch | Strong | Faint | Faint |
| Pit, distortion | Faint | Strong | Faint |
| Inclusion | Faint | Strong | Faint |
| Adhesion chip | Strong | Strong | Strong |
| Top surface dust | Strong | Faint | Faint |

Cross-referencing defect image intensity, combined with the defect's morphological properties (shape and intensity distribution within the image) provide a means for relatively accurate defect classification. With the present invention, some advantages over prior art inspection systems may be recognized. One advantage is that the invention can be applied to inspect a range of flat media: transparent (such as LCD glass), non-transparent reflective and non-transparent diffusing. Another advantage is that a glass inspection system according to the present invention can be used to detect all common defects occurring during LCD glass production. Furthermore, the invention provides means for a more cost effective inspection of flat media. Another advantage is multiple embodiments associated with different modes of inspection may be combined in a single inspection system. In current optical inspection, harmless, removable dust particles are notoriously confused with defects causing a false rejection of a good product, however, the current invention overcomes such false rejection. In yet a further advantage, the vision channels are very compact, which allows the invention to be installed in tight spots along the flat media production plant. Another advantage is that this level of performance is difficult and expensive to match by conventional imaging lenses.

Another advantage is that since the size of the defects are enlarged in the image, there is a reduced demand on detector resolution which also reduces the cost of the overall system.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A method of detecting a defect in a transparent media comprising the steps of:
    transmitting a collimated light beam from a light source to said transparent media;
    detecting said defect by scanning said transparent media as said collimated light passes through said transparent media; and
    forming an image of the defect directly on an image receiving media, based on light reflected off said defect, regardless of a position said defect in said transparent media
    transmitting said image to a film diffuser; and
    transmitting said image to an image detector via a Gradient Refractive Index lens array.

2. The method of claim 1 wherein a size of said image is calculated via a Kirchhoff-Fresnel, Fraunhoffer or other diffraction model.

3. The method of claim 1 wherein said step of transmitting said collimated light beam comprises the step of:
    transmitting a wavelength collimated light beam.

4. The method of claim 1 wherein said step of transmitting said collimated light beam comprises the step of:
    transmitting an incoherent collimated light beam.

5. The method of claim 1 wherein said light source and said image receiving media is above said transparent media.

6. The method of claim 1 wherein said light source is below said transparent media and said image receiving media is above said transparent media.

* * * * *